United States Patent [19]

Hawkins

[11] Patent Number: 4,778,510
[45] Date of Patent: * Oct. 18, 1988

[54] TRIAZONE FERTILIZER AND METHOD OF MAKING

[75] Inventor: Edwin F. Hawkins, Baton Rouge, La.

[73] Assignee: Triazone Corporation, Parsippany, N.J.

[*] Notice: The portion of the term of this patent subsequent to Nov. 19, 2002 has been disclaimed.

[21] Appl. No.: 46,648

[22] Filed: May 7, 1987

[51] Int. Cl.$^4$ .................... C05C 9/00; C05C 9/02; C07D 251/08
[52] U.S. Cl. ........................................ 71/30; 71/1; 71/11; 71/27; 71/64.1; 544/220
[58] Field of Search .................. 71/30, 1, 11, 27, 28, 71/29, 64.1; 544/220

[56] References Cited

U.S. PATENT DOCUMENTS 4,554,005 11/1985 Hawkins .................................. 71/30
4,599,102 7/1986 Hawkins .................................. 71/30

OTHER PUBLICATIONS

Hawkins (I), Inpadoc Database Abstract, U.S. Pat. No. 4,599,102, Jul. 8, 1986, filed Oct. 7, 1985.
Hawkins II, Inpadoc Database Abstract, U.S. Pat. No. 4,554,005, Nov. 19, 1985.

*Primary Examiner*—Richard A. Schwartz
*Attorney, Agent, or Firm*—William T. Hough

[57] ABSTRACT

In a preferred embodiment, a high-yield method producing novel water soluble triazone compositions having a typical analysis as follows, percentages being based on the total weight of the reaction product: urea at about 17.5%; MMU at about 3.4%; MDU at about 1.0%; HMT at about 4%; water soluble triazone at about 48%; produced by a novel method in which ammonia/HCHO mole ratio is about 0.3, and in which percentage ammonia added and reacted during the initial reaction is about 4.5% by weight of total reactants, initial cooking is for about 45 minutes, followed by final cooking for about 10 minutes, both initial and final cooking are at about 90 degrees Centigrade, at a nitrogen content of about 28%, at an initial cooking-pH maintained immediately after ammonia addition, at about pH 9, and at a lower pH during the final cooking resulting from termination of adding further potassium hydroxide, the optimum mole ratio during the process, of reactants urea, formaldehyde and ammonia, for example, being about 0.9:1:0.30; otherwise, the method is a two stage-cooking procedure in which urea and/or particular substituted urea is reacted with particular aldehyde(s) and ammonia and/or particular primary amine(s). Novel soluble triazone compositions include novel soluble triazone compounds made from ammonia or from amines such as 2-amino-2-methyl-1-propanol, tris(hydroxymethyl) amino methane, and 2-amino-2-ethyl-1,3 propanediol. Typical novel water-soluble triazone include 1-3, diethyl triazone, 1,3,4,5,6 pentamethyl triazone, 1-3 dimethyl triazone, 4-6 dimethyl triazone, 1,3 dimethyl, 5, hydroxyethyl triazone, 4,6 dimethyl, 5, hydroxyethyl triazone, and 4,6 diethyl triazone. These novel triazones are applied to crop foliage and/or vegetation foliage and/or sod, by liquid foliar spraying after conventional dilution of the product sufficiently for effective foliar spray, utilizing any desired and/or conventional spraying apparatus or machine.

28 Claims, No Drawings

TRIAZONE FERTILIZER AND METHOD OF MAKING

This invention is directed to a novel method for producing water-soluble triazones and to novel triazones and their use as foliar fertiliers.

BACKGROUND TO THE INVENTION

Prior to this invention, the present inventor was granted U.S. Pat. Nos. 4,554,005 and 4,599,102 granted Nov. 19, 1985 and July 8, 1986 respectively, directed to similar subject matter, namely novel water soluble triazone compositions and their methods of preparation.

While the inventions of those patents represented major advances in the art, it was desirable to obtain further novel water soluble triazone(s), of which it was not at all clear whether or not such compounds could or could not be produced, never having existed before. A particular reason for uncertainty in these matters is founded on the fact that these water soluble triazone compounds cannot be readily isolated in the dry state. Their existence or ability to exist and be effective as such, depends upon many variables inclusive of particular percentages present of the water soluble triazone(s) and of particular percentages of each of several other components of the final reaction product.

Also, toxicity to foliage of novel triazone(s) is not predictable, and likewise and accordingly no advance utility as a fertilizer, particularly as a foliar fertilizer can be predicted heretofore.

It has also been desirable to substantially increase the yield of the water soluble triazone compositions of the above-noted prior patents and of the present novel water soluble triazone compositions, since the method of production heretofore has been considered undesirable due to lower yields of water soluble triazone.

In that regard, based on the emperical equation of reaction of formaldehyde and ammonia and urea to form water soluble triazone(s), the molar ratio of urea/formaldehyde/ammonia would reasonably be expected to be 1/2/1.

Also, based on such emperical reaction equation for producing water soluble triazone(s), it would be reasonable to expect yield to decrease as either urea or formaldehyde each increased in relative amount(s) with regard to the one quantity thereof relative to two quantities of formaldehyde based on the emperical formula.

OBJECTS OF THE INVENTION

Accordingly, objects of the present invention include the obtaining of novel compositions and a novel method obtaining unexpectedly high yields of water soluble triazone(s) in the reaction product as compared to what was known or possible heretofore, and new use of novel compounds as fertilizers.

Another object is to ascertain whether there exist particular ranges of various ingredients, within such ranges unexpectedly improved yields are obtainable of water soluble triazones utilizable as fertilizers.

Another object is to ascertain whether among apparent equivalents for reactants, there exist particular ones that obtain unexpectedly improved yields, and if so, the particular ranges in which such improved yields may be achieved for water soluble triazones.

Another object is to ascertain and produce novel water soluble triazones having utility as fertilizer, particularly as foliar fertilizer, which novel triazones are not significantly nor fatally toxic to plants or foliage thereof.

Another object is to ascertain variations in the method of production of soluble triazones which significantly increase or alternatively decrease high yields of water soluble trizones.

Other objects become apparent from the preceding and following disclosure.

One and more objects are obtained by the invention as described herein.

SUMMARY OF THE INVENTION

Broadly, the invention may be described as a novel method obtaining unexpectedly high yield of triazone compositions of the above-noted patents and of the novel triazone compositions noted below, and the novel triazone compositions themselves best produced by this new method. Additionally the invention includes the method of applying these novel triazone compositions as fertilizer by foliar or other method of application, foliar application being made possible by virtue of the water soluble nature of the novel triazone compositions.

More particularly the inventive method movely has ascertained and utilizes a critical caustic to be utilized in adjusting or maintaining particular pH during initial reaction, as well as having ascertained novel ranges and ratios and operating temperature ranges and periods of reaction, each of which critically effect and obtain unexpectedly high and improved yield(s) of water soluble triazone(s) in a two stage method of initial heating of reactants, followed by a second stage of heating as follows. The method of producing water soluble triazone compositions of this invention and of the prior above-noted patents includes, within aqueous media, the initial cooking (reacting) of a urea-like component with an aldehyde and an ammonia-source reactant and/or an amine, while maintaining pH within a critical range by intermittent or continual addition of preferably potassium hydroxide within a critical range during initial cooking phase by adding potassium hydroxide in an amount within a critical range, and permitting pH to change by terminating potassium hydroxide addition during the second stage. Amount of potassium hydroxide critically required to be added, broadly ranges between about 0.5 percent and 1.8 percent by weight of total reactants, with the caustic being added in amount(s) sufficient to maintain during reaction of initial reactants the pH at about 8.6 to about 9.3; preferred results are obtained with a critical narrow preferred range from about 0.8 percent to about 1.4 percent by weight, with the caustic being added in an amount sufficient to maintain pH of initial reactants within a pH range of about 8.8 to about 9.1, depending on the particular urea/formaldehyde mole ratio. In addition to criticality of the pH, experimentation having established that preferred higher yields will be normally obtained within the preferred critical pH range, additionally also low yields will normally continue unless care is taken to maintain other variables also within narrow critical ranges as follow. In the initial reactants, the urea-like compound(s) relative to the aldehyde-like compound(s) has a molar weight ratio critically ranging broadly from about 0.65 to about 1.6, critically preferably from about 0.72 to about 0.95. Ammonia or ammonia-source(s) has a molar ratio of broadly critically form about 0.24 to about 0.40, preferably from critically about 0.25 to about 0.30, the ammonia (from ammonia or ammonia-source compound(s)). Whem ammonia is employed, it is preferably present at a weight percentage critically ranging from about 3.1 percent to about 5.6 percent, more preferably from about 3.3 to about 5 percent, on a weight basis of all reactants above-noted. The above-noted urea/aldehyde ratios are used within the pH ranges of about 8.6 to about 9.3, preferably critically from about 8.7 to about 9.1. Nitrogen source reactants are typically employed in amounts such that total nitrogen in the resulting triazone composition ranges from critically about 22.5 to about 32 percent, based on total weight of all reactants as previously set-forth above, and normally from about 26 to about 30 percent. Heating is at about 87–92, preferably 90.5–91.5 degrees C., for up to 70, preferably up to 60 minutes total.

During the initial stage, the caustic added to maintain pH is preferably KOH aqueous solution ranging from aqueous solution of about 10 to 55 percent, preferably aqueous solution of from about 40 to 50 percent, optimally an aqueous solution of about 45 percent. As a standard, a dilution normally commercially available, the above-noted amount (ranges) stated for the potassium hydroxide utilized in the method of the present invention, has been the conventional 45 percent aqueous solution; accordingly, if other aqueous dilutions-percentages of potassium hydroxide are alternatively employed, the above-specified critical employable-amounts (ranges) of aqueous potassium hydroxide would be interpolated to different equivalent ranges, not altering the nature of the invention. It has been experimentally ascertained that other aqueous caustics such as typically sodium hydroxide aqueous solution (NaOH aqueous solution) may be employed (the sodium hydroxide ranging from an aqueous solution of about 40 to 60 percent). However, improved higher yields of water soluble triazone might be obtained by the preferred use of the potassium hydroxide within the ranges specified above. Other caustics which likewise would obtain unexpected inferior yield typically would be expected to include other normally recognized equivalents such as sodium and/or lithium hydroxide and/or sodium carbonate or other strong caustic(s). Sodium hydroxide would have been expected to be the most likely equivalent as a substitute for potassium hydroxide, but such appears not to be the case, as well as experimentation having resulted in unexpectedly superior results obtained within preferred ranges of the neutralizing aqueous potassium hydroxide. As with the present inventor's above-noted prior triazone patents, the present novel method likewise maintains methylene diurea at an unexpectedly low and satisfactory minimum, noting that the larger the percentage of methylene diurea in the final reaction product, the lower the triazone compound yield as a part of the total weight of triazone composition-solution final reaction product, resulting from conducting the novel method within the plurality of critical parameters above-described.

In the preceding novel method, the ingredient-reactants and equivalents thereof are as follow. Urea-source reactants may be urea and/or substituted urea. The ammonia-source preferably is anhydrous ammonia, aqua ammonia, and/or a primary amine. The aldehyde source may be formaldehyde, acetaldehyde or substituted aldehydes or the like. Initial cook is about 20–55, preferably 40–50 min.; final cook is about 7–35, preferably 10–20 min. While the product of the above-noted novel method has been referred to as a triazone composition, it is not composed of solely merely a triazone compound, but is composed of a composite or aqueous solution of a plurality of different compounds, at least one of which is the particular triazone compound the preparation of which the novel method is directed. Accordingly, the triazone composition within the scope of this present and improved novel invention includes the following products in the broad and preferred ranges indicated. It should be noted that, as described before, the components of the final reacted product of the preceding novel method are all in and a part of an aqueous solution which, not being solid (dry) cannot be analyzed by prior typical nor known methods for separating and identifying triazone compounds and percentages thereof, since to dry the present composition would destroy the required balance in percentages and the equilibrium, to produce undesirable products unstable and/or insoluble, to defeat the utility of the inventive triazone composition. Thus, as set-forth for example in the inventor's prior U.S. Pat. No. 4,599,102 at column 8 thereof, lines 21 through 50, herewith incorporated by reference into this disclosure, the analytical method utilizing a high performance liquid chromatograph (designated as HPLC) was and is utilized to separate reactions products and to identify the same, also using paper chromatographic separation.

In the following table, MMU represents monomethylolurea and/or monomethylolurea-type compound(s), and MDU represents methylenediurea and/or methylenediurea-type compound(s), and DMU represents dimethylolurea and/or dimethylolurea-type compound(s), and HMT represents hexamethylenetetramine and/or hexamethylenetetramine-type compound(s).

Based on experimental results, typical components of the reaction products of respective broad and narrow ranges of the method of making of the present invention, are as follow in Table I.

TABLE I

PROJECTED TYPICAL PRODUCT ANALYSIS
Product component: Amount (wt. % of total aqueous soln. reaction pdt.)

| | Broad Range | Preferred Range |
|---|---|---|
| Urea: | about 9 to about 35 | about 11 to about 16 |
| MMU: | 0.0 to about 5.6 | about 0.5 to about 2.5. |
| MDU: | about 0.8 to about 1.5 | about 0.8 to about 1 |
| DMU: | about 0.6 to about 3.5 | about 0.6 to about 1.2 |
| HMT: | about 0.0 to about 5.25 | about 0.0 to about 2 |
| Triazone | about 42 to about 55(+) | about 45 to about 55(+) |

While for the present invention the triazone compounds produced (as a part of the triazone compositions) by the preceding novel and unexpectedly improved method(s) have basically the same emperical and structural formalae as set forth in the inventor's above-noted prior patents, that disclosure hereby incorporated by reference into this disclosure, some of those prior-stated preferred compounds have respective emperical and structural formulae as follow:

C$_3$H$_7$N$_3$O—5-S-tetrahydrotriazone:

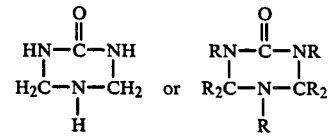

and C$_5$H$_{10}$N$_4$O$_3$—N-hydroxymethylformamide triazone:

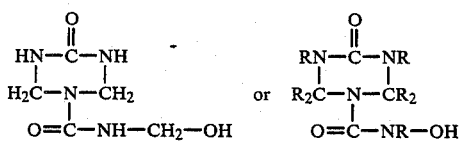

and $C_5H_{11}N_3O_2$—5-B-hydroxyethyltriazone:

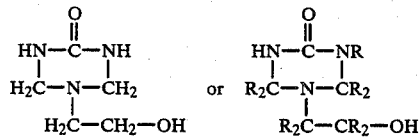

in which R is hydrogen, methyl, methylol, ethyl or ethylol. Another suitable triazone is one of the formula

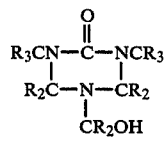

wherein R is defined as above.

Novel water-soluble triazone compounds newly produced as a part of novel triazone compositions produced by the method of this invention include:

1,3 dimethyl, 5, hydroxyethyl triazone—$C_7H_{15}N_3O_2$ of molecular weight of 173 and having 24.3% N:

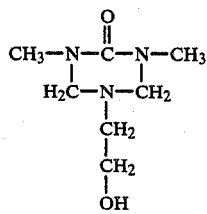

by the method of this invention utilizing principal reactant amounts of dimethyl urea, formaldehyde and monoethanolamine; and 4,6 dimethyl, 5, hydroxyethyl triazone—$C_7H_{15}N_3O_2$ having molecular weight of 205 and 20.5% N:

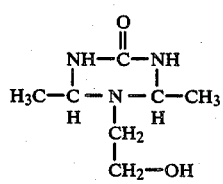

by the method of this invention utilizing principal reactant amounts of urea, acetaldehyde and monoethanolamine; and 4,6, diethyl, 5, hydroxyethyl triazone:

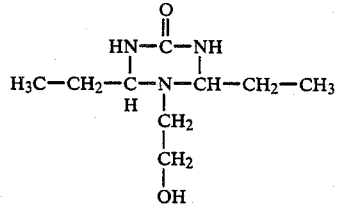

and likewise 1, 3 dimethyl, 5, hydroxyethyl, triazone, and 1-3 dimethyl triazone:

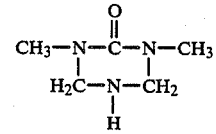

produced from dimethyl urea, formaldehyde and ammonia; and 4-6 dimethyl triazone:

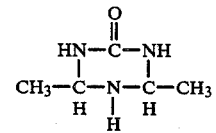

produced from urea, acetaldehyde and ammonia; and 4-6 diethyl triazone:

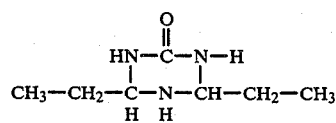

produced from urea, propionaldehyde, ammonia; and likewise 1, 3, 4, 5, 6, pentaethyl triazone, and 1,3,4,5,6 pentamethyl triazone:

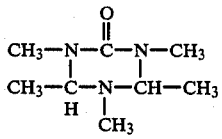

It should be noted that an integral part of the invention of these particular new triazone compounds as a part of the triazone compositions of the process of this invention, arise from the discovery that such compounds, as identified above, can be produced and are in-fact water-soluble in nature.

The above-identified novel compounds limited to water-soluble compounds of the generic formulas described-above and as follow, must necessarily at this point in time be prepared by the method of this invention, noting that these compound might possibly be produced also in lesser insignificant yields by the method of the above-noted prior patents of the inventor. However, until actual extensive experimentation by the present inventor, it was not possible to ascertain that these compounds could be produced nor that if produced that they would be soluble and stable (as to solubility and against breaking-up to form precipitates of other compounds), such being discerned solely by the above-noted identification procedure and observation of prepared solutions thereof as to shelf life and stability at varying storage temperatures and periods of time.

Other generic novel triazones produced by this improved claimed method of this invention are as follow:

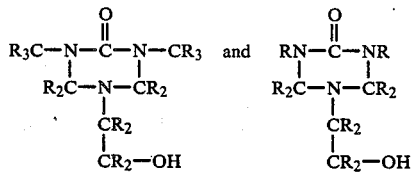

in which R is methyl or ethyl or non-carbon-substituted methyl or ethyl or hydrogen.

While with regard to the above-described method of preparation of triazones identified in my prior triazone patents above-noted as well as the novel triazone compositions of the present invention, the above-noted parameters are indeed controlling, an addition preferred critical limitation exists with regard to obtaining the unexpectedly high soluble triazone-compound yields of the present invention as follows.

It has been previously noted that the production of high yield appears to be dependent on the particular caustic employed to maintain pH control during the initial cooking stage, together with other process critical limitations and parameters. However, additionally it suprisingly has been discovered that for the highest possible yields by this invention for the soluble triazone compounds, that the time of initiation of the pH control is highly critical for preferred results in one embodiment of this improved inventive method, based on experimentation by the inventor, which experimentation confirms trend as controlled by that factor, as follow. See the following Table II.

The novel method includes the appropriate aqueous dilution of the reaction product, if any is desired or required to conform to conventional or desired manner of application, for the contemplated method of application to the soil, or sod, crop or other vegetation foliage, followed by appropriate deposit or application thereof.

However, an advantageous application arises by virtue of the high aqueous solubility and stability making possible easy use thereof by foliar spraying by either ground machines capable of spraying or by airplanes equipped to spray.

The novel methods of applying the fertilizer by mechanisms above-noted, of this invention are limited to the application of the above-noted novel water-soluble triazone compositions that include one or more of the novel water-soluble triazone compounds described above.

DETAILED DESCRIPTION

In the proceding novel method in the preparation of the triazone compositions containing the various above-described triazones of the preceding patents and of the present invention, in the place of formaldehyde (where used for triazone products formed from aldehyde), there may be substituted in part or in whole substituted aldehyd(s) such as acetaldehyde and/or propionaldehyde. It is to be recognized that the aldehyde is dissolved (soluble) in water or an appropriate non-reactive organic of any desired or conventional nature, known in the art. In substitution in part or in whole, for the ammonia, any primary amine or substituted primary amine may be used such as methyl amine, monomethanol amine, diethyl amine, amino methyl propanol, and the like.

It is redundant to repeat comments contained in my aforementioned patents on new triazone compositions and the novel triazones and methods of application thereof, with regard to the fact that is a combination of the present novel high aqueous solubility, high stability in solution, together with the low propensity to cause leaf-burn when applied directly to foliage, that sets these novel compounds and their use particularly in foliar application, apart from prior art. Propensity to cause foliar burning, while to some extent related in a direct proportion to degree of aqueous solubility, is not readily predictable, requiring laboratory and/or fieldexperimentation to ascertain whether or not a new compound or new composition inclusive of that new compound will or will not cause too much leaf burn as to be practical for use in a foliar spray. For the novel compound and compositions thereof above-described of the present invention, foliar burning has been found to be not a problemof any significant proportion, thereby giving utility to the present composition as a foliar spray and to the foliar spray method thereof.

Accordingly, the present method includes applying the novel compositions as fertilizer to soil, or to foliage of sod, crop(s), fruit vines and/or trees and/or other vegetation, preferably by foliar spraying thereof.

While above-noted critical limitations and parametershave been discussed with regard to the novel method obtaining unexpectedly high yields of the soluble triazone compounds of the triazone compositions of the inventor's aforementioned prior soluble triazone patents and of the present novel soluble triazones and compositions thereof, it has been found by experimentation that the yield and the preferred yield of the present inventive method of producing, is critically affected by the timing and method of pH control, as evidenced in the following Table II which also includes data showing the effect of decreasing ammonia on trends for lower or higher yields. As is typical, KOH is employed as commercially available aqueous 45% KOH, in the experiments of this invention.

TABLE II

| | Experiment | | | |
|---|---|---|---|---|
| | 9-1 | 9-2 | 9-3 | 9-4 |
| NH3/HCHO mole ratio | 0.3 | 0.3 | 0.3 | 0.3 |
| % NH3 | 4.9 | 4.9 | 4.9 | 4.6 |
| INITIAL COOK (min.) | 30 | 30 | 40 | 45 |
| FINAL COOK (degrees C.) | 10 | 10 | 0 | 10 |
| COOK TEMP. (degrees C.) | 90 | 90 | 90 | 90 |
| pH Control Point | 9.5 Begun as urea added | 9.5 Begun at end of ammonia addition | All added at beginning of initial cook | 9.0 |
| REACTION PRODUCT INGREDIENTS: | | | | |
| UREA | 18.3 | 18.7 | 16.3 | 16.9 |
| MMU | 5.4 | 5.5 | 4.0 | 6.0 |
| MDU | 1.6 | 1.9 | 3.8 | 0.8 |
| DMU | 0.4 | 0.5 | 0.6 | 0.5 |
| HMT | 2.8 | 2.7 | 2.8 | 10.7 |
| TRIAZONE | 32.0 | 32.5 | 23.6 | 24.1 |

TABLE II-continued

| | Experiment | | | |
|---|---|---|---|---|
| | 9-1 | 9-2 | 9-3 | 9-4 |
| compounds) | | | | | apart from lesser amounts of caustic having been added such that pH was maintained in experiments 9-1 and 9-2 at pH 9.5, the pH control began at different points in time, the experiment 9-1 beginning addition of caustic (potassium hydroxide) at the start of addition of urea urea-formaldehyde-85% solution), whereas in experiment 9-2 began at the end of addition of ammonia, with a resulting slightly larger yield of soluble traizone compound(s) in the experiment 9-2. In the experiment 9-3, an equivalent amount of caustic was all added rapidly at the beginning of the initial cook, with a resulting much lower yield of soluble triazone. It is a reasonable conclusion that the caustic must be added to maintain pH by initiating caustic addition only in a restricted or limited amount to the extent required for the maintaining of pH of the reaction media, from a time at least as early as the final addition of the last of the ammonia reactant, early addition of too much caustic clearly having an adverse effect on hopes of obtaining a high yield of soluble triazone compound(s).

In the experiment 9-4 (even though at a longer initial cook period), lower addition of ammonia, relative to the experiments 9-1, 9-2 and 9-3 viewed as a whole, appears to have an adverse effect resulting in the significantly lower yield, particularly in light of the experiment 9-3 having employed a more preferred pH and a preferred initial heating period. Also, 9-3, having zero final cook period, had lower triazone yield.

Greater light is shown on the experiment 9-4 by making reference to the additional experiments 9-4a through 9-4d all of which were conducted by the ammonia being employed in amounts sufficient to result in higher yields of water-soluble triazone, in the following Table III.

TABLE III

| | Experiment # | | | | |
|---|---|---|---|---|---|
| | 9-4a | 9-4b | 9-4c | 9-4d | 9-4e |
| $NH_3/HCHO$ mole ratio | 0.3 | 0.3 | 0.3 | 0.3 | 0.3 |
| % $NH_3$ | 4.9 | 4.9 | 4.9 | 4.9 | 4.9 |
| INITIAL COOK (min) | 45 | 45 | 45 | 45 | 45 |
| FINAL COOK (min.) | 10 | 10 | 10 | 10 | 10 |
| COOK TEMP. (degree C.) | 90 | 90 | 90 | 90 | 90 |
| pH CONTROL POINT | 9.0 | 9.0 | 9.0 | 9.0 | 9.0 |
| % PRODUCT INGREDIENTS: | | | | | |
| UREA | 16.8 | 17.8 | 17.9 | 16.8 | 16.7 |
| MMU | 3.2 | 4.2 | 4.9 | 4.6 | 3.5 |
| MDU | 1.7 | 2.0 | 2.1 | 1.0 | 0.9 |
| DMU | 0.3 | 0.3 | 0.5 | 0.5 | — |
| HMT | 1.9 | 1.6 | 1.6 | NEG. | 8.4 |
| TRIAZONE | 38.4 | 36 | 34.1 | 32.5 | 33.9 |

Accordingly it can be readily observed that as compared to the experiment 9-4, the triazone compound yields of experiments 9-4a through 9-4e exhibit significantly higher yield, as a trend, resulting from the higher ammonia reactant input of 4.9 as compared to the 4.6 of experiment 9-4.

Additionally, however, in the experiments 9-4c and 9-4d, aqueous 50% NaOH was substituted for aqueous 45% KOH, with the result that the triazone yields of experiments 9-4c and 9-4d are significantly lower than those of 9-4a and 9-4b, serving to point-out the critically improved results obtained by utilization of the potassium hydroxide as the caustic.

Also with regard to experiment 9-4e, this batch was produced on a much larger scale, i.e. larger production scale utilizing larger quantities of all reactants—serving to illustrate consistent results on a production scale, this batch being a 180 pound batch.

In another set of experiments, while not conducted at what eventually proved to be within all parameters of the method of this invention, the experiments nevertheless serve to demonstrate a trend-effect with regard to employment of varying percentage amounts of the KOH caustic, as illustrated in the following Table IV.

TABLE IV

| | Experiment # | | | |
|---|---|---|---|---|
| | 9A-1 | 9A-2 | 9A-3 | 9A-4 |
| $NH_3/HCHO$ mole ratio | 0.3 | 0.3 | 0.3 | 0.3 |
| % $NH_3$ | 4.9 | 4.9 | 4.9 | 4.9 |
| INITIAL COOK (min.) | 10 | 10 | 10 | 10 |
| FINAL COOK (min) | 15 | 15 | 15 | 15 |
| COOK TEMP. (degrees C.) | | | | |
| pH CONTROL POINT | 10.0–11.5 | 10.0–11.5 | 10.0–11.5 | 10.0–11.5 |
| % KOH Solution (45% KOH) | 1.7 | 1.5 | 1.5 | 2.0 |
| % PRODUCT INGREDIENTS: | | | | |
| UREA | 18.9 | 15.2 | 16.2 | 14.2 |
| MMU | 11.0 | 3.0 | 5.0 | 4.4 |
| MDU | 2.1 | 2.0 | 2.9 | 3.3 |
| DMU | 1.7 | 0.4 | 1.3 | 0.4 |
| HMT | 3.9 | 0.3 | 8.3 | 8.9 |
| TRIAZONE | 11.2 | 26.6 | 15.6 | 9.5 |

The Experiment was continued in Table V below.

TABLE V

| | Exper. # | | |
|---|---|---|---|
| | 9B-1 | 9B-2 | 9B-3 |
| $NH_3/HCHO$ mole ratio | 0.3 | 0.3 | 0.3 |
| % $NH_3$ | 4.9 | 4.9 | 4.9 |
| INITIAL COOK (min.) | 10 | 10 | 10 |
| FINAL COOK (min.) | 15 | 15 | 15 |
| COOK TEMP. (degrees C.) | 90 | 90 | 90 |
| pH CONTROL POINT | ALL AT pH 10.0 TO pH 11.5 | | |
| % KOH Solution (45% aqu. KOH) | 1 | 1.5 | 2 |
| % PRODUCT INGREDIENTS: | | | |
| UREA | 17.5 | 17.6 | 16.1 |
| MMU | 8.3 | 7.8 | 4.0 |
| MDU | 2.1 | 3.5 | 4.0 |
| DMU | 1.1 | 1.4 | 1.4 |
| HMT | 3.7 | 5.0 | 2.8 |
| TRIAZONES | 16.3 | 10.4 | 8.2 |

The foregoing experiments of Tables IV and V serve to illustrate several trends. Relative to the undesirably low initial and final cooking period times as shown, higher ammonia reactant up to a point, in this situation serves to actually increase yield of soluble triazone, but excessive amounts (exp. 9A-4/2% KOH, and exp. 9-3B/2% KOH) reverses trend, serving to inhibit or trend away from higher triazone compound yields, particularly at the higher cooking temperatures exceeding the parameters of this invention, particularly where the higher percentages of 1.5 and 2.0 are utilized as illustrated. The higher yields at the lower percentage of 1% serves to suggest again that moderate and gradual addition of KOH only in minimally effective quantities required to maintain the pH that has been ascertained to produce the highest yields, is the best and critical approach within the spirit of this invention, noting that the experiments 9B are all conducted within the critical temperature parameters of the present invention, although not within the critical reaction-period times for the initial and final cooking periods; thus, while trends may be observed, the triazone yield are not indicative of the high yields obtainable by this improved invention when all parameters are adhered to.

The following Table VI illustrates several experiments in which all parameters and limitations were maintained within the inventive ranges and requirements, illustrating the unexpectedly high yields of soluble triazones obtained thereby.

In the Table VI experiments, the values were substantially identical for the following constants; ammonia/HCHO mole ratio—0.3; percentage anhydrous ammonia by weight of total reactants (& water)—4.9; initial cook—45 minutes; second stage or final cook—10 minutes; temperature of initial and final cooks—90 degrees Centigrade (C), plus or minus 1; pH—9.0, plus or minus 0.3; and potassium hydroxide was the caustic utilized during the method.

TABLE VI

| REACTION PRODUCT | EXPERIMENT 3 | | |
|---|---|---|---|
| | 9C-1 | 9C-2 | 9C-3 |
| UREA | 17.0 | 17.5 | 18.0 |
| MMU | 0.7 | 3.4 | 3.2 |
| DMU | — | — | — |
| HMT | — | — | — |
| TRIAZONE | 46.9 | 48.0 | 42.0 |

From the Table VI triazone yields, it can be readily seen that the yields are remarkably high, resulting from the combination of critical limitations. While the triazone yield ranges between about 42 and 48, the typical yield of this ammonia input and molar ratio, the 9C-1 and 9C-2 had 47 to 48 yields as is further evidenced by the following Table VII in which the anhydrous ammonia-reactant is utilized at varying and higher levels.

For the experiments of Table VII, the values of reactants and conditions were identical to those of Table VI, except as otherwise shown or stated.

TABLE VII

| | EXPERIMENT 3 | | |
|---|---|---|---|
| | 9C-4 | 9C-5 | 9C-6 |
| % ANHYDROUS AMMONIA | 4.9 | 5.1 | 5.4 |
| Ammonia/HCHO mole ratio | 0.30 | 0.32 | 0.34 |
| REACTION PRODUCT: | | | |
| UREA | 7.4 | 8.9 | 9.5 |
| MMU | 2.0 | 2.1 | 1.9 |
| MDU | 1.1 | 1.3 | 1.5 |
| DMU | 2.4 | 2.5 | 3.3 |
| R.T. 7.11 (sub. triazone) | 10.3 | 8.9 | 6.1 |
| TRIAZONE | 49.5 | 53.3 | 53.7 |

TABLE VII-continued

| | EXPERIMENT 3 | | |
|---|---|---|---|
| | 9C-4 | 9C-5 | 9C-6 |
| R.T. 8.61 (unknown) | 2.8 | 2.7 | 1.9 |
| HMT | 3.0 | 3.5 | 5.0 |

From the Table VII it is readily seen that highly remarkable yields of water soluble triazones are obtained at the higher percentages of anhydrous ammonia reactant, provided that the other critical parameters and limitations of the present invention, are followed.

While for some occasional experiment, within a common series of experiments, will obtain a soluble triazone yield that for some unexplained reason or process defect comes-up far below the norm, and while likewise sometimes a random unexplainable high yield of soluble triazone turns-up even though the method of production is apparently the same as others of that or other series of experiments, the following experiments and tables thereof are of value in asceertaining trends and parameters for different variables, in relation to such trends; this is true even when one or more of the process values are not within the final parameters and/or limitations of the present invention, and most likely occur when there is some error in testing or in procedure.

For the following tables, accordingly, values while sometimes different for reactants or conditions where a constant is desired, where the values are moderately close to one-another, it is possible to draw valid conclusions for the affect of the real outstanding variables of the experiments being compared.

In the following Table VIII, the values and conditions of the process and product are identical as follows, unless otherwise stated: ammonia/HCHO molar ratio—0.3; percentage anhydrous ammonia—4.9; Initial and Final cooking temperatures—90 degrees C.; initial and final cooks are expressed in terms of minutes, and the caustic employed was potassium hydroxide.

TABLE VIII

| | EXPERIMENT # | | | | | | | | | |
|---|---|---|---|---|---|---|---|---|---|---|
| | 9D-1 | 9D-2 | 9D-3 | 9D-4 | 9E-1 | 9E-2 | 9E-3 | 9E-4 | 9E-5 | 9E-6 |
| INITIAL COOK: | 45 | 45 | 45 | 45 | 45 | 30 | 30 | 30 | 30 | 15 |
| FINAL COOK: | 10 | 10 | 10 | 0 | 0 | 15 | 15 | 10 | 0 | 10 |
| PH CONTROL: | 8.5 | 9.0 | 9.5 | 8.5 | 9.0 | 9.0 | 9.5 | 9.0 | 9.0 | 9.5 |
| REACTION PRODUCT % INGREDIENIS: | | | | | | | | | | |
| UREA | 20.1 | 17.5 | 17.6 | 16.5 | 17.3 | 16.1 | 17.3 | 17.8 | 18.0 | 16.5 |
| MMU | 1.2 | 3.4 | 3.3 | 4.7 | 6.2 | 5.2 | 6.0 | 5.2 | 7.4 | 8.8 |
| MDU | 1.5 | 1.3 | 1.4 | 1.1 | 1.3 | 2.0 | 1.3 | 1.3 | 0.9 | 1.1 |
| DMU | 0.4 | 0.3 | 0.3 | 0.4 | 0.5 | 0.5 | 0.5 | 0.4 | 0.8 | 1.0 |
| HMT | 3.7 | 1.5 | 9.6 | 1.3 | 2.2 | 1.6 | 3.0 | 2.5 | 3.2 | 3.4 |
| TRIAZONE | 39.2 | 44.8 | 36.7 | 40.3 | 38.9 | 37.9 | 32.3 | 37.0 | 35.2 | 25.3 |

From Table VIII it will be observed that the lower pH of 8.5 for each of 9D-1 and 9D-4 result in significantly lower triazone yield than the optimal pH 9.0 of 9D-2. It is also apparent that the low (15 minutes) Initial Cook heating (reaction) time of 9E-6 resulted in a substantially lower triazone yield pH 9.5 than the 9D-3, and likewise significantly lesser than the triazone yield at pH 9.5 of the 9E-3 experiment. Likewise for the 9E experiments, the pH 9.0 experiments of 9E-1, 9E-2, 9E-4 and 9E-5 each obtained higher triazone yields than the pH 9.5 experiments of 9E-3 and 9E-6. Also, the 45 minutes initial cooking supplemented by the final cooking of 10 minutes of 9D-2 obtained significantly greater yield than the 30 minute initial cooking (with 10 or 15 minute final cooking) of 9E-2, 9E-3, and 9E-4. In general from the 9D and 9E experiments, it may be said that soluble triazone yield tends to be higher at pH 9.0 as compared to each of pH 8.5 or 9.5, and that initial cooking time of 45 minutes obtains a higher yield of soluble triazone than 30 minutes or than 15 minutes, at least when there is a protracted period of further final heating and that lower cooking time for the final cooking, obtains poorer yield of soluble triazone at each of pH 9.0 and 9.5, at least.

Additional experiments along the same line were conducted as shown in the following Table IX, generally confirming the above-noted observations, together with shedding additional light as follows. Likewise, in these experiments 9F and 9G, the process conditions and limitations followed were identical to those of Table VIII, except as otherwise noted. For experiments 9F, the pH control point was pH 8.5, and for 9G the pH control point was pH 9.0, the latter pH 9.0 being within the parameters earlier set-forth for the present invention. As before, the initial and final cook periods are expressed in terms of minutes.

TABLE IX

| Exp. # | 9F-1 | 9F-2 | 9F-3 | 9F-4 | 9G-1 | 9G-2 | 9G-3 | 9G-4 | 9G-5 | 9G-6 | 9G-7 |
|---|---|---|---|---|---|---|---|---|---|---|---|
| I.CK. | 45 | 45 | 45 | 30 | 45 | 45 | 30 | 30 | 30 | 30 | 15 |
| F.CK. | 10 | 0 | 0 | 15 | 10 | 0 | 15 | 15 | 10 | 0 | 10 |
| UREA | 20.1 | 16.6 | 16.5 | 15.3 | 17.5 | 17.3 | 16.7 | 16.1 | 17.8 | 18.0 | 15.7 |
| MMU | 1.2 | 2.5 | 4.7 | 2.3 | 3.4 | 6.2 | 2.8 | 5.2 | 5.2 | 7.4 | 6.1 |
| MDU | 1.5 | 1.4 | 1.1 | 1.9 | 1.3 | 1.3 | 2.1 | 2.0 | 1.3 | 0.9 | 1.5 |
| DMU | 0.4 | 0.2 | 0.4 | 0.4 | 0.3 | 0.5 | 0.4 | 0.5 | 0.4 | 0.8 | 0.6 |
| HMT | 3.7 | 1.2 | 1.3 | 0.8 | 1.5 | 2.2 | 1.4 | 1.6 | 2.5 | 3.2 | 1.6 |
| TRIAZ. | 39.2 | 42.2 | 40.3 | 38.4 | 44.8 | 38.9 | 37.3 | 37.9 | 37.0 | 35.2 | 31.7 |

From the Table IX it is noted that solely the 9G-1 is totally within all critical parameters and limitations, that experiment showing the highest triazone yield of all the 9F and 9G experiments, being at pH 9 as compared to the 9F-1 at pH 8.5. Also as compared to the 9G-1 significantly higher yield, the lower initial cooking times of 9G-2 through 9G-7 all exhibited significantly lower yields at the same or higher pH levels of maintenance during initial cooking. Also, the only apparent differences in processes being time of final cooking for experiments 9G-1 and 9G-2, there is shown significantly greater yield of soluble triazone for 9G-1 at final cooking time of 10 minutes, as compared to the lesser yield of 9G-2 having a final cooking time of zero, and the same trend is found confirmed by comparing 9G-1 to 9F-2 for yield of soluble triazone. Even the comparison of 9G-5 to 9G-6 evidences the importance of there being the additional final cooking time, the yield of 9G-5 at 10 minutes final cooking trending toward greater soluble triazone yield than the zero final cooking time of 9G-6, even though both have the undesirably low initial cooking time of 30 minutes, this trend being consistent with the above preceding observation from other data. Even at zero final cooking time, the significant importance, as a trend, of the higher initial cooking period of minutes, is confirmed by consistent observations in comparing 9F-2 to 9G-6.

In comparison with the data and result in terms of soluble triazone of Table IX, data of experiments of the following Table X evidence the fact of poorer (lower) yields of soluble triazones at the higher pH 9.5 at the optimal initial and final cookings, as well as for non-optimal periods of cooking, and at the optimal 90 degree cooking as compared to the non-optimal 85 and 94 degrees C initial and final cookings. Even within the data of these experiments all at undesirably high pH 9.5, there is still evidenced consistent trends in yield of soluble triazone, such as optimal initial cooking time of 45 (when there is an additional final cooking time) of 9G-1 being consistently significantly greater in yield of soluble triazone than any of the other experiments at lesser initial cooking times.

Apart from the method of production of the novel soluble triazones of the present invention and the method of achieving the inventively high yields of those and other soluble triazones as described above, the method of making and steps thereof are the same as set-forth in the inventor's prior U.S. Pat. No. 4,599,102 at typically columns 10, 11, 12 and 14 thereof which are incorporated by reference into this disclosure.

In the experiments set-forth in the following Table X, a series of experiments were conducted utilizing aqueous sodium hydroxide as the neutralizing caustic during the method of preparation of the water soluble triazones, and for comparison therewith, utilizing an equivalent concentrations of potassium hydroxide, another series of experiments were conducted, in order to compare the relative selectivity of one caustic as compared to the other.

TABLE X

| Formulation (wt. %) | Exp. # | | | | | | | | | | |
|---|---|---|---|---|---|---|---|---|---|---|---|
| | 2-13 | 3-13 | 1-17 | 2-18 | 1-21 | 1-24 | 2-24 | 2-24A | 1-31A | 1-31B | 1-31C |
| Urea | 49.2 | 49.2 | 50.2 | 54.5 | 62.2 | 51.1 | 58.2 | 58.2 | 51.0 | 31.0 | 51.0 |
| Formald. | 26.7 | 26.7 | 27.9 | 16.9 | 19.4 | 28.3 | 18.1 | 18.1 | 28.3 | 28.3 | 28.3 |
| Ammonia (anh.) | 6.2 | 6.2 | 5.5 | 3.5 | 4.0 | 5.0 | 3.6 | 3.6 | 5.0 | 5.0 | 5.0 |
| NaOH (50 aq. soln.) | 1.0 | 1.0 | 1.0 | 1.8 | 1.4 | — | — | — | — | — | — |
| KOH (45% aq. soln.) | — | — | — | — | — | 1.6 | 2.0 | 2.0 | 1.2 | 1.2 | 1.2 |
| U/F/NH₃ | 0.9/ 1/ 0.4 | 0.9/ 1/ 0.4 | 0.9/ 1/ 0.35 | 1.6/ 1/ 0.36 | 1.6/ 1/ 0.36 | 0.9/ 1/ 0.31 | 1.6/ 1/ 0.35 | 1.6/ 1/ 0.35 | 1.6/ 1/ 0.35 | 0.9/ 1/ 0.32 | 0.9/ 1/ 0.32 | 0.9 1/ 0.32 |
| Procedure: | | | | | | | | | | | |
| pH (init.) cook | 9.0 | 9.0 | 9.0 | 9.0 | 9.0 | 9.0 | 9.0 | 9.0 | 9.0 | 9.0 | 9.0 |

TABLE X-continued

| Formulation (wt. %) | Exp. # | | | | | | | | | | | |
|---|---|---|---|---|---|---|---|---|---|---|---|---|
| | 2-13 | 3-13 | 1-17 | 2-18 | 1-21 | 1-24 | 2-24 | 2-24A | 1-31A | 1-31B | 1-31C | |
| Temp. (C.) | 90 | 90 | 90 | 90 | 90 | 90 | 90 | 90 | 90 | 90 | 90 | 90 |
| Cook Time: | | | | | | | | | | | | |
| Initial cook | 45 | 45 | 45 | 45 | 45 | 45 | 45 | 45 | 45 | 45 | 45 | |
| Final cook | 10 | 10 | 10 | 10 | 10 | 10 | 10 | 10 | 10 | 10 | 10 | |
| Product analysis: | | | | | | | | | | | | |
| urea | 23.5 | 23.4 | 19.0 | 34.4 | 36.7 | 18.3 | 37.0 | 37.3 | 16.2 | 17.2 | 17.7 | |
| triazone | 29.0 | 29.6 | 32.5 | 17.6 | 24.9 | 32.9 | 22.3 | 20.9 | 31.2 | 20.7 | 30.0 | |
| MMU | 0.6 | 1.6 | 1.9 | 1.6 | N.D.* | 1.2 | 0.9 | 1.3 | 2.1 | 2.0 | 2.0 | |
| DMU | 3.0 | 3.1 | 1.2 | 1.5 | 1.9 | 1.5 | 2.0 | 2.0 | 1.2 | 0.9 | 1.0 | |
| MDU | 0.8 | 0.6 | 0.4 | 1.0 | 1.0 | 0.5 | 1.0 | 0.8 | 0.4 | 0.3 | 0.3 | |
| HMT | N.D. | N.D. | N.D. | N.D. | N.D. | N.D. | N.D. | N.D. | N.D. | N.D. | N.D. | |

NOTE(*): N.D. — not detected.

From a study of the triazone yield of the preceding Table X, together with the comparison of yields of the sodium hydroxide-utilized experiments 2-13, 3-13, 1-17, 2-18 and 1-21, with the potassium hydroxide experiments 1-24, 2-24, 2-24A, 1-31A, 1-31B, and 1-31C, it appears that higher yields might be obtained across-the-board by the utilization of potassium hydroxide as the neutralizing caustic. Also, the potassium hydroxide group of experiments most often had the higher yields (in so far as trend goes) at the lower urea/formaldehyde weight ratio of 0.9 and the lower ammonia/formaldehyde weight ratio of 0.32 and 0.31, while concurrently the weight percentage of KOH did not exceed 1.6.

In a series of experiments, not here shown, comparing results with alternately anhydrous ammonia versus aqueous ammonia, at the time of addition during the practice of the method of this invention, it was ascertained that yield is not increased nor decreased by use of one instead of the other, for the produced water soluble triazone.

In another series of experiments of which two thereof utilized aqua ammonia, while the others used anhydrous ammonia (more convenient), the weight molar ratios of urea to formaldehyde were varied in some of the experiments, and the weight molar ratios of ammonia to formaldehyde were varied in some of the experiments, in order to further ascertain effects thereof on the yield of water soluble triazone in the method of this invention, all of these experiments utilizing potassium hydroxide as the caustic, the weight percentage (based on total weight of reactants) also being varied in some of the experiments. The amounts utilized for the variables, and the results thereof in the product produced, are shown in the following table XI.

TABLE XI

| Experiment | a | b | c | d | e | f | g | h | i | j | k | l |
|---|---|---|---|---|---|---|---|---|---|---|---|---|
| Formulation (wt. %): | | | | | | | | | | | | |
| Urea | 58.8 | 57.8 | 57.8 | 58.8 | 54.3 | 57.8 | 51.0 | 51.3 | 51.0 | 51.0 | 37.9 | 41.1 |
| Formaldehyde | 18.4 | 18.3 | 18.3 | 18.4 | 30.6 | 18.3 | 28.3 | 28.3 | 28.3 | 28.3 | 38.2 | 41.0 |
| Ammonia | 3.1 | 3.5 | 3.5 | 3.0 | 5.5 | 3.5 | 5.1 | 4.9 | 5.4 | 5.0 | 9.6 | 8.1 |
| KOH (45% soln) | 2.1 | 2.1 | 2.1 | 2.4 | 1.3 | 2.2 | 1.4 | 1.4 | 1.4 | 1.6 | 1.1 | 0.9 |
| U/F/NH3 | 1.6/1/0.33 | 1.6/1/0.34 | 1.6/1/0.34 | 1.6/1/0.29 | 0.9/1/0.32 | 1.6/1/0.34 | 0.9/1/0.32 | 0.9/1/0.30 | 0.9/1/0.34 | 0.9/1/0.31 | 0.5/1/0.44 | 0.5/1/0.35 |
| (mole ratio) | | | | | | | | | | | | |
| Procedure: | | | | | | | | | | | | |
| pH (Initial cook) | 9.0 | 9.0 | 9.0 | 9.0 | 9.0 | 9.0 | 9.0 | 9.0 | 9.0 | 9.0 | 9.0 | 9.0 |
| Temp. (C.) | 90 | 90 | 90 | 90 | 90 | 90 | 90 | 90 | 90 | 90 | 90 | 90 |
| Cook Time: | | | | | | | | | | | | |
| Initial | 45 | 45 | 45 | 45 | 45 | 45 | 45 | 45 | 45 | 45 | 45 | 45 |
| Final | 10 | 10 | 10 | 10 | 10 | 10 | 10 | 10 | 10 | 10 | 10 | 10 |
| Product Analysis: | | | | | | | | | | | | |
| Urea | 33 | 33.1 | 33.5 | 31.6 | 17.3 | 35.8 | 16.4 | 17.4 | 18.9 | 17.8 | 8.10 | 2.80 |
| Triazone | 23.5 | 21.8 | 22.4 | 23.1 | 28.1 | 25.3 | 35.4 | 34.4 | 35.2 | 29.5 | 21.9 | 33.4 |
| MMU | 2.0 | 1.5 | 1.6 | 1.9 | 3.0 | 1.4 | 1.9 | 2.3 | 1.7 | 4.2 | 1.4 | N.D. |
| DMU | 0.7 | 1.1 | 0.6 | 0.9 | 0.9 | 0.7 | 1.0 | 1.0 | 1.3 | 0.5 | 0.7 | 1.4 |
| MDU | 0.9 | 0.9 | 0.9 | 1.2 | 0.5 | 1.1 | 0.4 | 0.5 | 0.5 | 0.9 | 0.2 | 0.2 |
| HMT | 0.6 | 1.3 | 1.1 | 0.4 | 0.6 | 8.6 | 1.1 | 1.4 | 2.5 | 8.3 | 11.6 | 4.4 |

It should be noted that, as recognized by most researchers, that occasionally for some undetected defect or variation in procedure, a particular test or experiment that appears to be within all critical parameters, nevertheless fails to produce an acceptable product for some reason, or fails to produce an expected high yield of water-soluble triazone. That is the case with the experiment e which appears to be within desired parameters and amounts of reactants, but has resulted in an unexplainable low yield of 28.1% for the water soluble triazone, and this experiment does not follow overwhelming numbers of other experiment disclosed herein that evidence exceptionally high yields at such designated values of conditions, reactants, etc.; while the amount of ammonia employed at 5.5% during the method, is at the upper end of acceptable limits, it is believed some other undetected factor detrimentally affected yield in this experiment.

From a comparison of experiments in Table XI, it is observed that experiments a, b, c, d and f each have too high a level of potassium hydroxide, at 2.1, 2.1, 2.1, 2.4, and 2.2 respectively, and yields of water-soluable triazone each trend lower than experiments e and g through l which have lower acceptable amounts of KOH added during the neutralizing process. Note that k used lower urea reactant. While all ammonia/formaldehyde ratios of all experiments a through l are within critically acceptable ranges, the amount (%) of ammonia (by weight of total reactants) is excessively high (above acceptable limits) for experiments k and l, and within acceptable limits for experiments f, g, h and i. It will be moreover noted, that for experiments f, h, g and i (in that order of increasing amounts of ammonia) at 3.5, 4.9, 5.1, and 5.4 percents respectively, there is a trend of increasingly higher yield of water-soluble triazone.

Finally, as to Table XI it will again be observed that there is no ascertainable difference caused in yield as affected by use of alternately either of aqua ammonia or anhydrous ammonia.

In another series of experiments, upper limits of various parameters of reactants were further evidenced as follow as illustrated in the following Table XII.

From Table XII it will be observed that for the experiment "a" thereof, the ratio of ammonia to formaldehyde at 0.4 far exceeded allowable maximum critical limits, while also the ratio of urea to formaldehyde at 0.6 was below minimum critical limit, while the employed amount of KOH was at its upper limit, the combined effect resulting in a significantly reduced water-soluble triazone yield. For the experiment "b" thereof, the amount of KOH at 1.5% was near its upper limit, together with the amount of ammonia at 5.7 was exceeding its critical upper limit, with the combined effect being the significantly reduced yield of water-soluble triazone. The amount of KOH for each of experiments c, d, e and f thereof each far exceeded the upper critical limit of allowable amount of KOH, resulting in significantly lower yields of water-soluble triazone.

An additional series of experiments were conducted in which different experiments varied temperatures of cooking times, varied pH, varied ratio of ammonia to formaldehyde, varied ammount of ammonia, and varied the amount of KOH, with the result that definite trends in yields are ascertainable for the water-soluble triazone, as shown in the following Table XIII.

TABLE XII

| Experiments | a | b | c | d | e | f |
|---|---|---|---|---|---|---|
| Formulation (wt. %): | | | | | | |
| Urea | 41.7 | 50.1 | 51.0 | 51.7 | 56.7 | 58.5 |
| Formaldehyde | 34.8 | 31.3 | 28.3 | 25.8 | 23.7 | 18.3 |
| Ammonia | 7.9 | 5.7 | 5.1 | 4.7 | 4.3 | 3.3 |
| KOH(45% soln.) | 1.6 | 1.5 | 2.0 | 2.0 | 2.2 | 2.7 |
| U/F/NH$_3$ | 0.6/ 1/ | 0.8/ 1/ | 0.9/ 1/ | 1.1/ 1/ | 1.2 1/ | 1.6 1/ |
| Mole wt. ratio | 0.4/ | 0.32/ | 0.32 | 0.32 | 0.32 | 0.32 |
| Procedure: | | | | | | |
| pH (Initial cook) | 9.0 | 9.0 | 9.0 | 9.0 | 9.0 | 9.0 |
| Temp. (entire cook) (C.) | 90 | 90 | 90 | 90 | 90 | 90 |
| Cook Times (min.): | | | | | | |
| Initial | 45 | 45 | 45 | 45 | 45 | 45 |
| Final | 10 | 10 | 10 | 10 | 10 | 10 |
| Product analysis (wt.): | | | | | | |
| Urea | 14.8 | 15.6 | 19.5 | 21.8 | 28.5 | 37.2 |
| Triazone | 32.7 | 32.1 | 30.8 | 30.7 | 30.0 | 22.8 |
| MMU | 1.6 | 2.8 | 2.2 | 1.7 | 1.6 | 0.9 |
| DMU | 0.8 | 0.7 | 0.5 | 0.7 | 0.7 | 0.9 |
| MDU | 0.4 | 0.5 | 0.9 | 0.6 | 0.7 | 0.9 |
| HMT | N.D. | N.D. | N.D. | N.D. | N.D. | N.D. |

TABLE XIII

| Exper.: | a | b | c | d | e | f | g | h | i | j | k | l |
|---|---|---|---|---|---|---|---|---|---|---|---|---|
| Formulat. (wt %): | | | | | | | | | | | | |
| Urea | 37.5 | 41.1 | 37.7 | 37.9 | 38.3 | 37.6 | 37.6 | 41.3 | 41.0 | 41.7 | 40.5 | 40.5 |
| Formald. | 37.5 | 41.0 | 37.7 | 38.2 | 38.3 | 37.6 | 37.6 | 34.4 | 35.0 | 34.8 | 33.8 | 33.8 |
| Ammonia | 5.3 | 8.1 | 7.7 | 9.6 | 9.9 | 10.6 | 10.6 | 5.2 | 6.7 | 7.9 | 8.7 | 8.7 |
| KOH (45% soln) | 0.6 | 0.9 | 0.7 | 1.1 | 0.6 | 0.5 | 0.8 | 0.7 | 0.7 | 1.6 | 0.7 | 0.5 |
| U/F/NH$_3$ | 0.5/ 1/ .25 | 0.5/ 1/ .35 | 0.5/ 1/ .36 | 0.5/ 1/ .44 | 0.5/ 1/ .45 | 0.6/ 1/ .50 | 0.6/ 1/ .50 | 0.6/ 1/ .27 | 0.6/ 1/ .34 | 0.6/ 1/ .40 | 0.6/ 1/ .45 | 0.6/ 1/ .45 |
| Procedure: | | | | | | | | | | | | |
| pH (Initial cook) | 9.2 | 9.0 | 8.7 | 9.0 | 8.7 | 8.7 | 8.7 | 8.7 | 8.7 | 9.0 | 8.7 | 8.7 |
| Temp. (C.) (entire cook) | 91 | 90 | 91 | 90 | 91 | 91 | 91 | 91 | 91 | 90 | 91 | 91 |
| Cook Time: | | | | | | | | | | | | |
| Initial | 30 | 45 | 30 | 45 | 15 | 30 | 45 | 30 | 15 | 45 | 30 | 45 |
| Final | 10 | 15 | 10 | 10 | 10 | 10 | 15 | 10 | 10 | 10 | 10 | 15 |
| Product analysis (wt %): | | | | | | | | | | | | |
| Urea | 3.9 | 2.8 | 4.6 | 8.1 | 5.8 | 10.7 | 24.5 | 5.3 | 8.2 | 14.8 | 12.5 | 23.2 |
| Triaz. | 34.9 | 33.4 | 37.8 | 21.9 | 38.7 | 33.4 | 34.4 | 38.3 | 35.7 | 32.7 | 37.0 | 18.1 |
| MMU | 3.8 | N.D. | 2.3 | 1.4 | 2.5 | 1.5 | 1.7 | 3.9 | 2.6 | 1.6 | 0.8 | N.D. |
| DMU | 0.9 | 1.4 | 6.0 | 0.7 | N.D. | 0.8 | N.D. | 2.7 | 8.6 | 0.8 | 0.9 | N.D. |
| MDU | 1.1 | 0.2 | N.D. | 0.2 | 0.6 | 0.5 | 1.3 | 0.9 | N.D. | 0.4 | 0.5 | 1.2 |
| HMT | 6.9 | 4.4 | N.D. | N.D. | 0.7 | 13.4 | 22.8 | N.D. | 2.9 | N.D. | 8.4 | 17.2 |

Preceding Table XIII discloses further trends in yields of water-soluble triazone as dependent upon various parameters, as follow. For each of experiments a, b, c, e, f, g, h, i, k, and l, the amount of KOH employed was significantly below the lower critical limit. Except for experiments a and h thereof, in all other experiments ammonia is too high. For b–g and i–k, ammonia molar ratio is too high. Exp. h is closest to acceptable ranges, and has one of the higher yields. Exp. i has too short an initial cook. The high percentage of HMT was unacceptable for each of experiments a, e–g, k and l and too high MMU in g.

In all experiments of this disclosure, anhydrous ammonia was utilized, unless otherwise specified.

Further experiments were conducted in an attempt to further ascertain method ranges in amounts and conditions favorable to obtaining improved high yields of water-soluble triazone, as set-forth in Table XIV as follows.

TABLE XIV

| Experim. # | a | b | c | d | e | f | g | h | i | j |
|---|---|---|---|---|---|---|---|---|---|---|
| Formulation (wt. %): | | | | | | | | | | |
| Urea | 47.7 | 46.5 | 46.2 | 46.2 | 51.8 | 49.7 | 50.1 | 49.4 | 46.3 | 48.0 |
| Formaldehyde | 31.7 | 30.9 | 30.7 | 30.7 | 32.4 | 31.1 | 31.3 | 31.0 | 29.0 | 35.6 |
| Ammonia (anhyd.) | 4.9 | 5.5 | 7.8 | 7.8 | 4.6 | 4.9 | 5.7 | 6.0 | 7.7 | 8.0 |
| KOH (45% soln) | 0.8 | 0.5 | 0.7 | 1.5 | 0.8 | 0.9 | 1.6 | 0.9 | 0.8 | 1.0 |
| U/F/NH$_3$ M. Ratio | .75/1/.27 | .75/1/.34 | .75/1/.45 | .75/1/.45 | .75/1/.25 | .75/1/.28 | .75/1/.32 | .75/1/.34 | .75/1/.47 | .75/1/.47 |
| Procedure: | | | | | | | | | | |
| pH (Initial cook) | 8.7 | 8.7 | 8.7 | 8.7 | 8.7 | 8.7 | 9.0 | 8.7 | 8.7 | 8.7 |
| Temp (C.)/entire ck. | 91 | 91 | 91 | 91 | 91 | 91 | 90 | 91 | 91 | 91 |
| Cook time: | | | | | | | | | | |
| Initial | 30 | 15 | 30 | 45 | 30 | 30 | 45 | 15 | 30 | 45 |
| Final | 10 | 10 | 10 | 15 | 10 | 10 | 10 | 10 | 10 | 15 |
| Product analysis (wt. %): | | | | | | | | | | |
| Urea | 11.8 | 13.4 | 16.0 | 25.9 | 11.0 | 10.3 | 15.6 | 12.8 | 18.8 | 24.0 |
| Triazone | 47.1 | 45.9 | 35.5 | 25.6 | 37.1 | 48.0 | 32.1 | 21.7 | 32.8 | 29.3 |
| MMU | 3.6 | 2.6 | 1.5 | 4.4 | 6.8 | 3.4 | 2.8 | 2.5 | 1.1 | N.D. |
| DMU | 0.7 | N.D. | 1.0 | N.D. | 1.2 | 0.8 | 0.7 | N.D. | 1.1 | N.D. |
| MDU | 0.9 | 0.9 | 0.6 | 1.1 | 0.6 | 0.9 | 0.5 | 0.7 | 0.5 | 1.1 |
| HMT | 1.5 | 2.0 | 6.4 | 13.6 | 0.4 | 1.3 | N.D. | 2.7 | 7.1 | 9.7 |

From the preceding Table XIV it is noted that the products of experiments c, d, i and j each contained unacceptably high levels of HMT, and product of experiment e contained an unacceptably too high level of MMU. Experiments d and j products contained unacceptably too high levels of unreacted urea. High water-soluble triazone yields of experiments a, b and f resulted from all reactants and added amount of KOH and ratios and method conditions and reactions times, etc. each and all being within acceptable parameters of this invention, experiment a obtaining a yield of 47.1 and experiment b obtaining a yield of 45.9 and experiment f obtaining a yield of 48% by weight of total reaction product. The experiments c, d, g, h, i and j each utilized unacceptably high amounts of ammonia reactant, contributing to low yield of water-soluble triazone. Experiments c, d, i and j each utilized an unacceptably high molar ratio of ammonia relative to formaldehyde, contributing to low yield of water-soluble triazone; experiment d had an ammonia molar ratio above the preferred range, relative to formaldehyde, contributing to low triazone yield. Experiments b and h each utilized an unacceptably low initial period of cook of merely 15 minutes, contributing to a lower yield of water-soluble triazone; in that regard, it will be noted that the good (elevated) yield (45.9%) of water-soluble triazone of experiment b accordingly is nevertheless lower than the triazone yields of experiments a (47.1%) and f (48.0) both of which had initial cook periods of 30 minutes; it is also noted that while the triazone yield of experiment b was relatively high, the fact of its being lower that yields of experiments a and f also resulted at-least in-part from the amount of KOH added during the method, being below acceptable range for normal good result—for example see Table XIII's experiments a and h which obtained poor triazone yields at such low amounts of KOH. Amounts of added KOH were unacceptably too high for each of Table XIV's experiments d and g, contributing to low triazone yield.

An additional series of experiments were conducted to further illustrate the affects of varying amounts, ratios, conditions, etc. on water-soluble triazone yields, as shown in the following Table XV.

TABLE XV

| Experim. | a | b | c | d | e | f | g | h | i | j | k | l | m | n |
|---|---|---|---|---|---|---|---|---|---|---|---|---|---|---|
| Formulation (wt. %) | | | | | | | | | | | | | | |
| Urea | 52.0 | 51.7 | 54.1 | 51.0 | 51.0 | 50.2 | 49.2 | 54.2 | 56.4 | 53.9 | 51.7 | 50.3 | 53.7 | 53.- |
| Formald. | 28.8 | 28.7 | 30.0 | 28.3 | 28.3 | 27.8 | 27.2 | 27.1 | 28.2 | 27.0 | 25.8 | 25.2 | 26.9 | 26.- |
| Ammonia | 4.2 | 4.9 | 5.5 | 5.1 | 5.4 | 6.0 | 6.2 | 3.9 | 4.4 | 5.0 | 4.7 | 5.4 | 6.0 | 6.6 |
| KOH (45%) | 1.0 | 1.0 | 1.1 | 2.0 | 1.4 | 1.0 | 0.9 | 1.1 | 0.9 | 1.4 | 2.0 | 1.2 | 2.3 | 0.6 |
| U/F/NH$_3$ (Mole Ratio) | .9/1/.26 | .9/1/.30 | .9/1/.32 | .9/1/.32 | .9/1/.34 | .9/1/.38 | .9/1/.40 | .9/1/.25 | .9/1/.28 | 1.0/1/.32 | 1.0/1/.32 | 1.0/1/.38 | 1.0/1/.39 | 1.0/1/.43 |
| Procedure: | | | | | | | | | | | | | | |
| pH (Initial cook) | 8.7 | 8.7 | 8.7 | 9.0 | 9.0 | 8.7 | 8.7 | 8.7 | 8.7 | 8.7 | 9.0 | 8.7 | 9.0 | 8.7 |
| Temp. (C.)/entire cook | 91 | 91 | 91 | 90 | 90 | 91 | 91 | 91 | 91 | 91 | 90 | 91 | 91 | 91 |
| Cook Time (min.) | | | | | | | | | | | | | | |
| Initial | 30 | 30 | 15 | 45 | 45 | 30 | 30 | 30 | 15 | 15 | 45 | 30 | 45 | 30 |
| Final | 10 | 10 | 10 | 10 | 10 | 10 | 10 | 10 | 10 | 10 | 10 | 10 | 10 | 10 |
| Product Analysis: | | | | | | | | | | | | | | |
| Urea | 16.0 | 16.8 | 15.4 | 19.5 | 18.9 | 20.6 | 19.5 | 20.5 | 18.7 | 20.0 | 21.8 | 21.1 | 25.9 | 26.3 |
| Triazone | 44.2 | 42.0 | 40.1 | 30.8 | 35.2 | 34.7 | 35.6 | 33.6 | 35.0 | 37.3 | 30.7 | 36.1 | 33.7 | 36.3 |
| MMU | 4.3 | 3.8 | 3.0 | 2.2 | 1.7 | 2.4 | 1.9 | 4.2 | 9.2 | 2.9 | 1.7 | 1.8 | 3.2 | 1.8 |
| DMU | N.D. | 0.6 | 0.9 | 0.5 | 1.3 | 0.3 | 1.1 | 0.8 | 0.4 | 0.6 | 0.7 | 1.0 | ND | ND |
| MDU | 1.1 | 1.2 | 0.9 | 0.9 | 0.5 | 1.5 | 0.6 | 1.1 | 0.6 | 0.8 | 0.6 | 0.3 | 1.0 | 1.3 |
| HMT | ND | 1.5 | 0.5 | ND | 2.5 | 2.9 | 4.1 | 0.3 | ND | 0.8 | ND | 3.2 | 6.2 | 5.1 |

From Table XV, it will be seen that for the experiments a and b thereof, all parameters, conditions, amounts, ratios, etc. of the critical limitations were fulfilled, resulting in the good yields of 44.2% and 42.0% respectively, as compared to the others of series c through g. The initial cooking time of experiments c, i and j, was an unacceptably low 15 minutes, resulting in reduced yield of water-soluble triazone, the product of experiment i as well having an unacceptably high amount of MMU. The amount of KOH employed for experiments d, k, m and n was unacceptably high or low, resulting in the low yields of 30.8, 30.7, 33.7 and 36.3 of the water-soluble triazones; resulting products of g, m and n also included such high values of HMT (at 4.1 and 6.2 respectively) that the product was not a viable product. The ratio of ammonia to formaldehyde was unacceptably high in each of experiments e, f, g, l, m and n, contributing to unacceptably low yields of water-soluble triazones. The experiment n utilized KOH in an unacceptably low amount, below the critical limits of the present invention, contributing to a low yield of 33.6.

A further group of experiments were conducted to further identify critical parameters, particularly with regard to amount of KOH and with regard to molar ratio of ammonia to formaldehyde, as set-forth in the following Table XVI.

TABLE XVI

| Exper. # | a | b | c | d | e | f | g | h | i | j | k | l |
|---|---|---|---|---|---|---|---|---|---|---|---|---|
| Formulat. (wt. %): | | | | | | | | | | | | |
| Urea | 61.5 | 61.2 | 58.1 | 56.7 | 57.3 | 58.3 | 61.1 | 62.6 | 60.4 | 56.6 | 56.6 | 60.1 |
| Formald. | 25.6 | 25.5 | 24.2 | 23.7 | 23.9 | 24.3 | 21.8 | 22.3 | 21.6 | 20.4 | 0.5 | 19.0 |
| Ammonia | 3.2 | 3.2 | 3.4 | 4.3 | 4.6 | 6.5 | 3.1 | 3.8 | 4.2 | 4.5 | 4.5 | 4.6 |
| KOH (45%) | 0.9 | 0.8 | 1.3 | 2.2 | 1.5 | 0.6 | 1.6 | 1.3 | 1.5 | 1.3 | 1.1 | 1.1 |
| U/F/NH$_3$ | 1.2 | 1.2 | 1.2 | 1.2 | 1.2 | 1.2 | 1.4 | 1.4 | 1.4 | 1.4 | 1.4 | 1.4 |
| (Molar Ratio) | 1/ .22 | 1/ .22 | 1/ .25 | 1/ .32 | 1/ .34 | 1/ .43 | 1/ .25 | 1/ .30 | 1/ .34 | 1/ .39 | 1/ .39 | 1/ .43 |
| Procedure: | | | | | | | | | | | | |
| pH (Ini.k.) | 8.7 | 8.7 | 8.7 | 9.0 | 8.7 | 8.7 | 8.7 | 8.7 | 8.7 | 8.7 | 8.7 | 8.7 |
| Temp. (C.) (entire Ck) | 91 | 91 | 91 | 90 | 91 | 91 | 91 | 91 | 91 | 91 | 91 | 91 |
| Cook Time: | | | | | | | | | | | | |
| Initial | 15 | 30 | 30 | 45 | 30 | 30 | 30 | 15 | 30 | 30 | 45 | 30 |
| Final | 10 | 10 | 10 | 10 | 10 | 10 | 10 | 10 | 10 | 10 | 10 | 10 |
| Product Analysis: | | | | | | | | | | | | |
| Urea | 23.9 | 23.2 | 25.7 | 28.5 | 29.5 | 32.8 | 31.4 | 30.5 | 31.3 | 33.2 | 44.1 | 38.0 |
| Triazone | 26.7 | 32.4 | 42.8 | 30.0 | 39.7 | 30.1 | 40.2 | 33.8 | 34.8 | 30.0 | 11.7 | 30.7 |
| MMU | 11.2 | 9.0 | 4.2 | 1.6 | 1.4 | 0.5 | 3.4 | 2.1 | 1.2 | 1.5 | N.D. | 0.7 |
| DMU | 3.2 | 3.1 | 1.0 | 0.7 | N.D. | N.D. | 1.0 | 0.7 | N.D. | 1.4 | N.D. | 0.3 |
| MDU | 1.6 | 2.0 | 1.3 | 0.7 | 0.9 | 1.1 | 1.4 | 1.1 | 1.0 | 0.3 | 1.9 | 1.1 |
| HMT | N.D. | 1.0 | 0.4 | N.D. | 1.6 | N.D. | 0.4 | 1.4 | 2.7 | 8.9 | 8.0 | 3.5 |

In above Table XVI, ratio of mole of ammonia to formaldehyde were each too low, below critical preferred minimum, for examples a, b, c and g, and too high, above the critical preferred maximum for each of examples f, j, k and l, resulting in low yields of water-soluble triazone. Amount of KOH was also below critical minimum amount in each of examples a, b and f, and likewise too high, above maximum critical range, in each of examples d, g and i, resulting in low yield of water-soluble triazone. Examples a and h each utilized initial cooking times below the critical minimum, resulting in low yields of water-soluble triazone. Being outside of critical parameters additionally caused unacceptably high amounts of unreacted urea in examples f and j, and unacceptably high amounts of MMU in examples a and b, and an unacceptably high amount of MDU in example b, and unacceptably high amounts of HMT in each of examples f and k. The example c, which had ammonia ratio to formaldehyde at 0.25, such being near the critical minimum of the lower end of the critical range, did not have a high yield, but otherwise was within all other critical parameters, etc. and had the highest yield of any of these experiments of Table XVI.

Additional experiments were conducted and are shown in Table XVII as follow.

TABLE XVII

| Examples | a | b | c | d | e | f | g |
|---|---|---|---|---|---|---|---|
| Formulation (wt. %) | | | | | | | |
| Urea | 60.7 | 63.7 | 58.5 | 62.6 | 57.1 | 57.2 | 60.8 |
| Formaldehyde | 19.0 | 19.9 | 18.3 | 19.4 | 17.8 | 17.9 | 19.0 |
| Ammonia | 2.7 | 3.4 | 3.3 | 3.8 | 4.1 | 4.1 | 4.6 |
| KOH (45%) | 1.7 | 1.4 | 2.7 | 1.1 | 1.2 | 2.4 | 1.1 |
| U/F/NH$_3$ (Mole Ratio) | 1.6/ 1/ .25 | 1.6/ 1/ .30 | 1.6/ 1/ .32 | 1.6/ 1/ .34 | 1.6/ 1/ .41 | 1.6/ 1/ .41 | 1.6/ 1/ .43 |
| Procedure: | | | | | | | |
| pH (Initial cook) | 8.7 | 8.7 | 8.7 | 9.0 | 8.7 | 8.7 | 8.7 |
| Temp. (C.) | 91 | 91 | 91 | 90 | 91 | 91 | 91 |
| Cook time: | | | | | | | |
| Initial | 30 | 30 | 45 | 30 | 30 | 45 | 30 |
| Final | 10 | 10 | 10 | 10 | 10 | 15 | 10 |
| Product Analysis: | | | | | | | |
| Urea | 34.1 | 31.5 | 37.2 | 36.5 | 35.4 | 40.5 | 39.6 |
| Triazone | 35.7 | 45.8 | 22.8 | 34.1 | 24.1 | 22.6 | 25.8 |
| MMU | 3.4 | N.D. | 0.9 | 1.3 | 0.6 | N.D. | 0.6 |
| DMU | 0.9 | 0.4 | 0.9 | 0.4 | 1.6 | N.D. | 0.3 |
| MDU | 1.4 | 1.2 | 0.9 | 1.1 | 0.4 | 1.5 | 1.2 |
| HMT | N.D. | 0.9 | N.D. | 1.4 | 0.9 | 4.2 | 4.4 |

From Table XVII is will be observed that massive amounts of urea are employed, such as in example b, at 63.7% by weight of total reactants, as also reflected in the molar ratio of U/F at 1.6, of that Table XVII; at this elevated level of urea, the upper allowable limit of maximum amount of KOH is increased to about 1.5, but above that level the higher yield of water-soluble triazone is adversely affected to cause a lower yield as evidenced by experiment "a" thereof. Concurrently, however, it appears that at these high urea that the upper maximum limit of ammonia/formaldehyde ratio is lowered below 0.34 to a maximum of about 0.31, noting that the experiment d thereof at ammonia/formaldehyde ratio of 0.34 resulted in a low yield or water-soluble triazone. The ammonia/formaldehyde ratio for each of experiments e, f and g of this table, were above the critical maximum upper limit, contributing to or causing the low yield of water-soluble triazone. Likewise, the high amounts of KOH, well above critical maximum allowable amount, for each of the experiments a, c, e, f and g of this table, resulted in low yields of water-soluble triazone, moreover noting that the high amounts of HMT in the products of experiments f and g made those products further unsatisfactory and unacceptable. Accordingly, within the altered allowable parameters for high amounts of urea as evidence in this table, the experiment b obtained the improved high yield of this invention.

From numerous of the preceding tables, it is further observed that the preferred yields of this invention are obtained at cook temperatures of about 91 degrees Centigrade, making the preferred critical temperature range from about 90.5 to about 91.5 degrees Centigrade, to obtain improved yields when other parameters of this invention are properly observed.

As noted above, it has not been possible to predict which water-soluble triazone products, if produced, would or would not be detrimental to plant life, particularly for a foliar fertilizer—a primary utility of the water-soluble triazones of this invention. In confirmation of that fact, it was observed that there existed agronomic diversity between the following triazones having the same molecular weight—namely 1,3 Dimethyltriazone and 4,6 Dimethyltriazone having the following structural formuli:

1,3 Dimethyltriazone:
  Molecular weight: 129

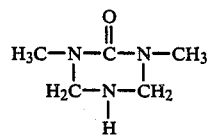

4,6 Dimethyltriazone:
  Molecular weight: 129

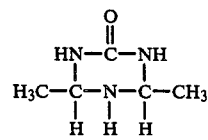

These products were evaluated on turf in Florida as shown in the following Table XVIII and in New Jersey as shown in the following Table XIX. Urea was included as a commonly used turf nitrogen source.

For purposes of the tables below, 1,3 Dimethyltriazone is abbreviated as 1,3 DMT, and 4,6 Dimethyltriazone is abbreviated as 4,6 DMT. Likewise, St. Augustine is abbreviated as S.A., and Bermuda 419 as Ber.. "Leaf Burn" (Rating, note b) is abbreviated as L.B.1, "Leaf Burn" (Rating, note d) as L.B.2, "Color Rating c" as Col.3, "Color Rating e" as Col.4, Color Rating f" as Col.5, and pounds of nitrogen per 1000 square feet is abbreviated as Lbs.. "Growth Rate" is abbreviated as G.R.

TABLE XVIII

| Test# | RES | Composition | Lbs. | L.B.1 S.A. | L.B.1 Ber. | Col.3 S.A. | Col.3 RES |
|---|---|---|---|---|---|---|---|
| 1 | 22252 | Urea | 1.5 | 1.83 | 1.83 | 2.00 | 0.50 |
| 2 | 22286 | 1,3 DMT | 1.5 | 3.5 | 4.00 | 2.00 | 0.00 |
| 3 | 22287 | 4,6 DMT | 1.5 | 1.33 | 2.17 | 2.33 | 2.17 |
| 4 | 22252 | Urea | 3.0 | 3.17 | 2.5 | 2.00 | 0.00 |
| 5 | 22286 | 1,3, DMT | 3.0 | 4.00 | 5.00 | 2.00 | 0.67 |

TABLE XVIII-continued

| Test# | RES | Composition | Lbs. | L.B.1 S.A. | L.B.1 Ber. | Col.3 S.A. | Col.3 RES |
|---|---|---|---|---|---|---|---|
| 6 | 22287 | 4,6 DMT | 3.0 | 2.17 | 3.17 | 2.5 | 3.50 |
| 7 | 22252 | Urea | 6.0 | 3.33 | — | 2.5 | — |
| 8 | 22286 | 1,3 DMT | 6.0 | 5.00 | — | 2.5 | — |
| 9 | 22287 | 4,6 DMT | 6.0 | 3.00 | — | 3.5 | — |

Footnotes:
a. (Treatment) Treatments applied to St. Augustine on 5/5/85 and to Bermuda on 5/16/85, clear, no rain until 5/20/85. Maximum temperature between 90-95 degrees F. each day following application. Spray volume of 4 gal/1000 sq. ft.. Plot size: 40 inches by 30 feet (100 sq. ft.)
b. (LB1) Rating scale 0 to 5: 0 - no burn to 5 - maximum burn. Average of 3 observations made 6 days after application.
c. (Col.3) Rating scale of 0 to 5: 0 - pale, chlorotic condition to 5 - deep green color. Average of 3 observations made 6 days after treatment.

TABLE XIX
(Evaluation of Nitrogen Sources on Bluegrass Turf at Allentown, NJ - 1985)

| Test # | RES | Composition | Lbs. | L.B.2 | Col.4 | Col.5/G.R. |
|---|---|---|---|---|---|---|
| 1 | 22252 | Urea | 1.5 | 2.0 | 4 | 2 |
| 2 | 22286 | 1,3 DMT | 1.5 | 4.0 | 2 | 1 |
| 3 | 22287 | 4,6 DMT | 1.5 | 1.0 | 4 | 3 |
| 4 | 22252 | Urea | 3.0 | 3.0 | 5 | 4 |
| 5 | 22286 | 1,3 DMT | 3.0 | 4.5 | 3 | 3 |
| 6 | 22287 | 4,6 DMT | 3.0 | 2.0 | 5 | 5 |
| 7 | 22252 | Urea | 6.0 | 4.0 | 5 | 5 |
| 8 | 22286 | 1,3 DMT | 6.0 | 5.0 | 3 | 4 |
| 9 | 22287 | 4,6 DMT | 6.0 | 4.0 | 4 | 4 |

Footnotes:
d. (Treatment) Treatments applied on 8/1/85, clear low 80's degrees F., no rain for at least 5 days. Spray volume - 4 gal/1000 sq. ft.. Plot size 40 inches by 30 feet (100 sq. ft.).
e. (LB2) Rating scale 0 to 5: 0 - no burn to 5 - maximum burn. Rating taken 8/6/85.
f. (Col.4) Rating scale 0 to 5: 0 - pale, chlorotic conditions to 5 - deep green color.
g. (Col.2) See c.

The data from the two precedings Tables XVIII and XIX each and both illustrate the diverse field characteristics of these two products. The 4,6 Dimethyltriazone is a safe, low burn, effective turf nitrogen source. In contrast, the 1,3 Dimethyltriazone is an undesirable nitrogen source for turf because of its high burn potential. This latter product has characteristics more like a foliage desiccating agent, rather than or as opposed to a nitrogen-source fertilizer for which it has no utility.

In all experiments of this disclosure, anhydrous ammonia was utilized, unless otherwise specified.

It is within the scope of this invention to make variations and modifications and substitution of equivalents as would be apparent to a person of ordinary skill in this art.

I claim:
1. A method for producing high yields of soluble triazone, comprising in combination: employing initial reactants comprising a urea-type compound-source, an aldehyde-type compound-source, an ammonia-type compound-source, and a solubilizing amount of water for said reactants, in which the urea-type compound-source, relative to the aldehyde-like compound(s), has a first molar weight ratio ranging from about 0.65 to about 1.6, and in which the ammonia-type compound-source, relative to the aldehyde type compound-source, has a second molar ratio of from about 0.24 to about 0.40, the method comprising the steps of initially heating said initial reactants for an initial reaction period of from about 20 minutes to about 55 minutes while during said initial reaction period, adding from about 0.75 percent to about 2.5 percent by weight potassium hydroxide in an amount sufficient to maintain pH of said initial reactants at a pH of from about 8.6 to about 9.3, said heating being sufficient to maintain said initial reactants at a temperature of from about 87 degrees Centigrade to about 92 degrees Centigrade, to produce cooked reactants, and substantially immediately thereafter followed by a final heating of said cooked reactants at said temperature for a final cooking period of from about 7 minutes to about 35 minutes while substantially terminating addition of said caustic, provided that the sum of said initial reaction period and said final cooking period being up to about 70 minutes, and substantially permitting pH to vary by substantially terminating addition of further caustic during said final cooking period, reaction of said reactants during said initial reaction period and said final cooking period being sufficient to form an aqueous solution of at least one soluble triazone of the formulae of the group consisting of:

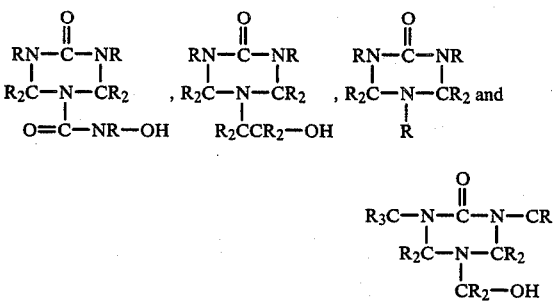

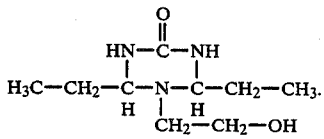

in which R is hydrogen, methyl, ethyl, methylol, or ethylol.

2. A method according to claim 1, in which said first molar weight ratio is from about 0.72 to about 0.95, and in which molar weight ratio of said ammonia type compound-source/said aldehyde type compound-source ranges from about 0.25 to about 0.30, and in which said initial reaction period ranges from about 40 minutes to about 50 minutes, and in which said final cooking period is from about 10 minutes to about 20 minutes, said sum being up to about 60 minutes, and said caustic being added during said initial reaction period in an amount sufficient to maintain pH at from about pH 8.7 to about 9.1, and in which said initial reaction period is at from about 90.5 degrees Centigrade to about 91.5 degrees Centigrade.

3. A method of claim 1, in which addition of said caustic during said initial reaction period, is commenced at substantially the end of adding ammonia type compound-source to the others of said initial reactants, and addition of said caustic is added at any one or more points in time up to an amount sufficient to maintain said pH.

4. A soluble triazone compound entitled 1,3, di-methyl, 5, hydroxyethyl triazone having the emperical formula $C_7H_{15}N_3O_2$ and structural formula of:

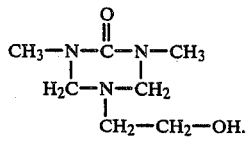

5. A soluble triazone compound entitled 4,6,dimethyl, 5, hydoxyethyl triazone having the emperical formula $C_7H_{15}N_3O_2$ and having a structural formula:

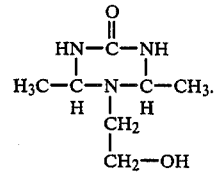

6. A soluble triazone compound entitled 4,6, diethyl, 5, hydroxyethyl triazone having the emperical formula $C_9H_{19}N_3O_2$ and having a structural formula:

$$\begin{array}{c} O \\ \| \\ HN-C-NH \\ | \quad\quad | \\ H_3C-CH_2-C-N-C-CH_2-CH_3. \\ H \;\; | \;\; H \\ CH_2-CH_2-OH \end{array}$$

7. A soluble triazone composition comprising the soluble triazone composition in aqueous solution, identified and produced by the method of claim 1, having a soluble triazone yield of at-least about 40 percent by weight of total aqueous solution reaction product.

8. A soluble triazone composition of claim 7, in which said yield is at-least about 42 percent by weight of total aqueous solution reaction product.

9. A soluble triazone composition comprising the soluble triazone composition in aqueous solution, identified and produced by the method of claim 2, having a soluble triazone yield of at-least about 40 percent by weight of total aqueous solution reaction product.

10. A soluble triazone composition of claim 9, in which said yield is at-least 42 percent by weight of total aqueous solution reaction product.

11. A soluble triazone composition comprising the soluble triazone composition in aqueous solution, identified and produced by the method of claim 3.

12. A method of fertilizing plants by foliar spraying comprising foliar spraying an aqueous solution of a composition according to any of claims 7 through 11.

13. A method of fertilizing plants by foliar spraying comprising foliar spraying an aqueous solution of a soluble triazone of any of claims 4 through 6.

14. A method of claim 1, in which said ammonia-type compound source comprises at-least a major and predominant proportion of ammonia, and employing said ammonia at a weight percentage ranging from about 3.1 percent to about 5.6 percent on a weight basis of all reactants and of water at time of reaction.

15. A method of claim 2, in which at-least a major and predominant proportion of said ammonia-type compound source consists essentially of ammonia, and employing said ammonia at a weight percentage ranging from about 3.1 percent to about 5.6 percent on a weight basis of all reactants and of water at time of reaction.

16. A method of claim 3, in which said ammonia-type compound source consists of ammonia, and employing said ammonia at a weight percentage ranging from about 3.1 percent to about 5.6 percent on a weight basis of all reactants and of water at time of reaction.

17. A method of claim 16, in which said ammonia type compound source is employed, relative to the aldehyde-like compound(s), in said second molar weight ratio ranging from about 0.25 to about 0.30.

18. A method of claim 1, in which said ammonia type compound source is employed, relative to the aldehyde-like compound(s), in said second molar weight ratio ranging from about 0.25 to about 0.30.

19. A water-soluble triazone compound entitled 1,3, dimethyl, 5, hydroxyethyl triazone.

20. A water-soluble triazone compound entitled 1,3,4,5,6, pentamethyl triazone.

21. A water-soluble triazone compound entitled 1,3, dimethyl triazone.

22. A water-soluble triazone compound entitled 4,6, dimethyl triazone.

23. A water-soluble triazone compound entitled 4,6, diethyl triazone.

24. A water-soluble triazone compound entitled 1,3, diethyl triazone.

25. A water-soluble triazone compound entitled 1,3,4,5,6, pentaethyl triazone.

26. A triazone composition comprising the soluble triazone composition in aqueous solution, identified and produced by the method of any of claims 14 through 18.

27. A method of claim 1, including during said initial heating, adding said potassium hydroxide in an amount ranging between about 0.5 and about 1.8 percent by weight.

28. A method of claim 1, including during said initial heating, adding said potassium hydroxide in an amount ranging between about 0.8 and about 1.4 percent by weight.

* * * * *